US00PP09992P

United States Patent [19]

Kientzler

[11] Patent Number: Plant 9,992

[45] Date of Patent: Aug. 5, 1997

[54] IMPATIENS PLANT NAMED 'ANGUILLA'

[75] Inventor: Ludwig Kientzler, Gensingen, Germany

[73] Assignee: Paul Ecke Ranch, Inc., Encinitas, Calif.

[21] Appl. No.: 621,216

[22] Filed: Mar. 25, 1996

[51] Int. Cl.[6] ..... A01H 5/00

[52] U.S. Cl. ..... Plt./87.6

[58] Field of Search ..... Plt./87.6

*Primary Examiner*—Howard J. Locker

*Attorney, Agent, or Firm*—Foley & Lardner

[57] ABSTRACT

A new and distinct cultivar of Impatiens plant named Anguilla, characterized by its large (7.0–7.5 cm) bright magenta flowers with fuchsia colored eyes; compact growth habit with excellent branching; early flowering and very floriferous habit; shiny, dark green foliage, and its adaptability to 4" pot, 6" pot, and 8" hanging basket culture.

1 Drawing Sheet

The present invention relates to a new and distinct cultivar of plant known as Impatiens and commercially known as New Guinea Impatiens. The new cultivar is known by the cultivar name Anguilla, and was developed by the inventor Ludwig Kientzler in Gensingen, Federal Republic of Germany by crossing the cultivar designated F G 561 (seed parent) with the cultivar H H 879 (pollen parent).

Asexual reproduction by terminal (stem tip) cuttings taken by or under the supervision of the inventor at Gensingen, Federal Republic of Germany, has shown that the unique features of this new impatiens are stabilized and are reproduced true to type in successive propagations.

The following characteristics distinguish the new impatiens from both its parent varieties and other cultivars of this general type known and used in the floriculture industry:

1. Unique flower color, large, bright magenta flowers with fuchsia colored eyes.
2. Compact growth habit with excellent branching characteristics. Plants in 16.5 cm pots were 17 cm tall and 36 cm wide, when plants were in full flower.
3. Early flowering and very floriferous. Plants were in flower 6 weeks after planting. Numerous large 7–7.5 cm flowers covered the plant surface.
4. Shiny, dark green foliage.
5. Well suited to 4" pot, 6" pot and 8" hanging basket culture.

Anguilla is similar in certain respects to Guadeloupe, a cultivar of the inventor disclosed in pending application Ser. No. 08/620,957. Anguilla has a leaf color similar to but not as dark as Guadeloupe. In addition, Anguillar has a more compact growth habit and blooms earlier than Guadeloupe. Further, as above noted, flower color of Anguilla is unique among other known cultivars of New Guinea Impatiens. These differences are based on comparisons made in May 1995 based on plants of the same age and in full flower.

The accompanying colored photographic drawing, is a top perspective view of the new cultivar, showing color as true as it is reasonably possible to obtain in a colored reproduction of this type.

The following is a detailed description of the new impatiens cultivar based on plants grown under commercial practice in Encinitas, Calif. Plants were started as rooted cuttings and were transplanted in mid-Feb. into 16.5 cm (6.5 inch) pots, one pot per plant. By mid-April, plants were growing vigorously and were in flower. The values, measurements and observations noted below were taken from plants in full bloom in mid-May.

Color references are made to The Royal Horticultural Society Colour Chart (R.H.S.), except where general terms of ordinary dictionary significance are used.

Parentage: Cross between F G 561 (seed) and H H 870 (pollen).

Asexual reproduction:

*Cutting type.*—Tip, with stems 2–3 cm long and developing to 4–5 cm after 21 days in propagation.

*Time to initiate roots.*—8–10 days at 23° C.; nicely developed root mass in 18–21 days.

*Rooting habit.*—Numerous, fibrous, adventitious roots from the stem.

Plant description:

*Form.*—Symmetrical, bush shaped, flowering herb, with self-branching characteristics giving the plant a full appearance. Pinching is not recommended since it does not enhance branching and only delays flowering by removing flower buds.

*Habit of growth.*—Vigorous, self-branching habit, producing whorls of leaves and flowers. Growth is indeterminate and flowering is continuous.

*Foliage description.*—Leaves are simple. Lower leaves on stems in whorls of 2–3. Higher on stem, leaves in whorls of mostly 5. Leaf shape: Broadly elliptic to ovate. Leaf blade tips are acuminate; bases of immature leaves are acute, mature leaves attenuate. Leaf blade size: Mature leaves 8–10 cm long and 3–4 cm wide. Petiole length: 2–2.5 cm. Leaf margin: Ciliated and finely serrated. Leaf texture: Slightly rugose. Upper surface: Glabrous. Under surface: Glabrous. Leaf color: Dark green with a red midvein. Upper surface: Leaves near 147A. Midvein near 53C. Under surface: Greyed purple, 183A-B. Venation: Pinnate.

Flowering description:

*Flowering habits.*—Very floriferous. Flowering is continuous. Flowers develop progressively around the whorl of leaves, taking 5–7 days from buds which show color, to bloom. Flowers are single and large, lasting for 2–3 weeks.

*Natural flowering season.*—Flowering is indeterminate and occurs throughout the year. Quantity of flowers increases with increasing light intensity and duration. However, floriferousness may wane during hot summer days in temperate climates.

*Flower buds.*—Ellipsoidal and covered with three (3) sepals plus rudimentary sepals fused into the under surface of the superior petal. A spur originates from the base of the inferior sepal. Spur is red and about 5 cm long.

*Flowers borne.*—Singly, on red pedicels 5–6 cm long.

*Quantity of flowers.*—One flower per leaf. Flowers occur progressively around the whorl of leaves so that tight buds to mature flowers are visible at the same time.

*Petals.*—Petals open less than perpendicular to the pedicel so that the plane of the flower surface is slightly cupped.

*Number of petals.*—Five (5) petals, all overlapping.

*Shape.*—All petals are heart-shaped. Superior petal has a broad base. Other petals have a pointed base.

*Color.*—Bright magenta with a fuchsia eye. Upper surface: Redder and darker than 57A. Fuchsia eye near 74A. Under surface: Near 58B.

*Flower size.*—Large up to 7.5 cm in diameter.

*Reproductive organs.*—Stamens: Five (5), broad and fused to form a tube around the ovary; red in color. Anther: Hooded and cream colored. Pollen: Cream colored. Stigma: Five-pointed star, colorless. Styles: Very short. Ovary: Five-celled, 4–5 mm long until fertilized. Grows to 1 cm or longer after fertilization; purplish-green in color.

Resistance to disease: Good resistance to common stem and root diseases, Rhizoctonia and Pythium. Botrytis may be a problem in humid or mist propagation environments, but no greater than with other New Guinea Impatiens cultivars.

It is claimed:

1. A new distinct cultivar of Impatiens plant named Anguilla, as illustrated and described.

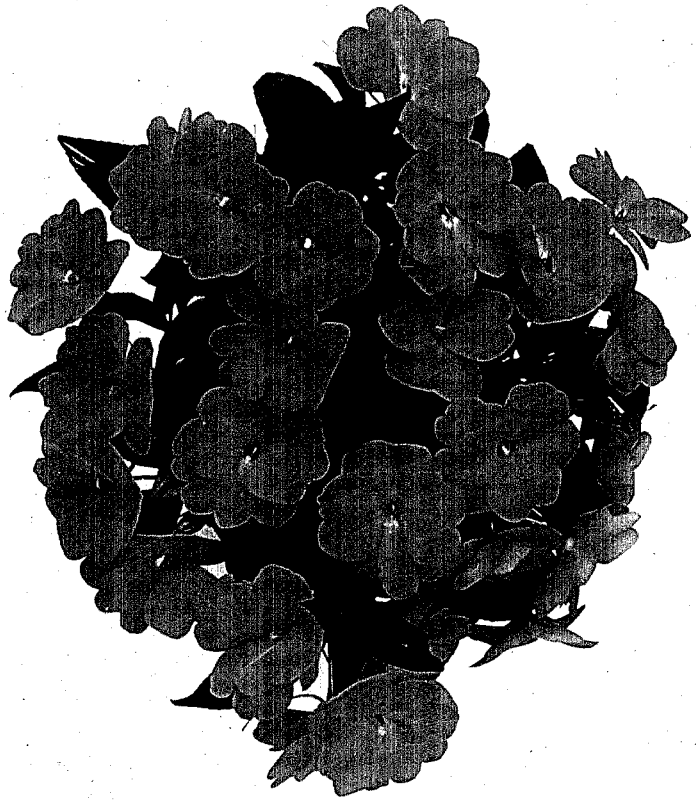

* * * * *